United States Patent
Nilsson et al.

(10) Patent No.: US 8,071,367 B2
(45) Date of Patent: Dec. 6, 2011

(54) SELECTING, CULTURING AND CREATING LINEAGE COMMITTED HEMATOPOIETIC STEM CELLS

(75) Inventors: Susan Kaye Nilsson, East Bentleigh (AU); David Norman Haylock, Melbourne (AU)

(73) Assignee: Commonwealth Scientific and Industrial Research Organisation, Clayton, Victoria (AU)

(*) Notice: Subject to any disclaimer, the term of this patent is extended or adjusted under 35 U.S.C. 154(b) by 531 days.

(21) Appl. No.: 11/913,141

(22) PCT Filed: Apr. 20, 2006

(86) PCT No.: PCT/AU2006/000529
§ 371 (c)(1),
(2), (4) Date: Apr. 25, 2008

(87) PCT Pub. No.: WO2006/116793
PCT Pub. Date: Nov. 9, 2006

(65) Prior Publication Data
US 2009/0215083 A1    Aug. 27, 2009

Related U.S. Application Data

(60) Provisional application No. 60/678,047, filed on May 4, 2005.

(51) Int. Cl.
*C12N 5/0789* (2010.01)
*C12N 5/074* (2010.01)
*C12N 5/078* (2010.01)

(52) U.S. Cl. .................................. 435/325; 530/388.7

(58) Field of Classification Search .................. None
See application file for complete search history.

(56) References Cited

U.S. PATENT DOCUMENTS

| | | | |
|---|---|---|---|
| 2005/0276793 A1* | 12/2005 | Milhem et al. | 424/93.7 |
| 2006/0115898 A1* | 6/2006 | Zhang et al. | 435/372 |
| 2006/0205071 A1* | 9/2006 | Hasson et al. | 435/366 |
| 2009/0215083 A1* | 8/2009 | Nilsson et al. | 435/7.21 |

FOREIGN PATENT DOCUMENTS

| | | |
|---|---|---|
| JP | 2003-189843 | 7/2003 |
| WO | WO 2005/007799 | 1/2005 |
| WO | WO 2005/105985 | 11/2005 |
| WO | WO 2006/045064 | 4/2006 |

OTHER PUBLICATIONS

JP 2003-189843, published Jul. 8, 2003, English translation accessed Feb. 25, 2010.*
Iwata et al., "Human marrow stromal cells activate monocytes to secrete osteopontin, which down-regulates Notch1 gene expression in CD34+ cells" Blood, 103(12):4496-4502 (Jun. 16, 2004).
Nilsson, et al. Osteopontin, a key component of the hematopoietic stem cell niche and regulator of primitive hematopoietic progenitor cells. 2005, Blood, vol. 106, No. 4, pp. 1232-1239.
Szilvassy, et al. Homing and engraftment defects in ex vivo expanded murine hematopoietic cells are associated with downregulation of beta1 integrin. Exp Hematol. Dec. 2001;29(12):1494-502.
Yokosaki, et al. The integrin alpha(9)beta(1) binds to a novel recognition sequence (SVVYGLR) in the thrombin-cleaved amino-terminal fragment of osteopontin. J Biol Chem. Dec. 17, 1999;274(51):36328-34.

* cited by examiner

*Primary Examiner* — Daniel C Gamett
(74) *Attorney, Agent, or Firm* — Karl Bozicevic; Bozicevic, Field & Francis LLP

(57) ABSTRACT

The present invention provides a method for selecting hematopoietic stem cells (HSCs) comprising providing an agent which binds to α9β1 integrin on the cell surface to a population of cells including HSCs and separating HSCs by virtue of the binding agent. The invention also provides a method of culturing a population of HSCs in the presence of an agent which binds to α9β1, wherein the agent inhibits differentiation of the HSCs. The invention also provides a method of producing a population of lineage committed cells comprising culturing HSCs in the presence of an agent which inhibits or prevents binding to α9β1.

7 Claims, 4 Drawing Sheets

SEQUENCE LISTING

<160> NUMBER OF SEQ ID NOS: 1

<210> SEQ ID NO 1
<211> LENGTH: 7
<212> TYPE: PRT
<213> ORGANISM: homosapien

<400> SEQUENCE: 1

Ser Val Val Tyr Gly Leu Arg
1               5

SELECTING, CULTURING AND CREATING LINEAGE COMMITTED HEMATOPOIETIC STEM CELLS

FIELD OF THE INVENTION

The invention relates to the modulation of the binding of integrin α9β1 present on hematopoietic stem cells to any of its ligands. In a specific aspect, it relates to the isolation, mobilization and expansion of Hematopoietic stem cells using integrin α9β1.

BACKGROUND OF THE INVENTION

The bone marrow provides a unique environment for multipotential and committed cells. It contains both structural and humoral components that have yet to be successfully duplicated in culture. The marrow cavity itself is a network of thin-walled sinusoids lined with endothelial cells. Between the walls of bone are clusters of hematopoietic cells and fat cells constantly fed by mature blood cells entering through the endothelium. Differentiated cells ready to function within the circulatory system depart the cavity in a similar fashion.

Hematopoietic stem cells (HSC) are the most primitive cells of the hematopoietic lineage, and have the ability to give rise to all cells of the hematopoietic lineage (including HSC). HSC are known to reside in the bone marrow, but their specific niche within the bone marrow microenvironment is not currently defined. Previous studies have established that certain HSC progeny, the lineage-restricted clonogenic hematopoietic progenitor cells (HPC), conform to a well-defined spatial distribution across the axis of the femur with greatest numbers near the central longitudinal vein. Such observations foster the widely held belief that the distinct spatial organization exhibited by these various cell populations within the bone marrow is a manifestation of specific adhesive interactions occurring with the underlying stromal tissue. However, due to the rarity of HSC and the lack of a single, unique antigenic marker allowing their unambiguous identification in situ, it has not been possible to define the spatial distribution of HSC within the bone marrow.

Evidence now exists to suggest that hematopoiesis is localized to the bone marrow by developmentally regulated adhesive interactions between primitive HSC and the stromal cell mediated microenvironment. It is likely that the adhesive interactions in this microenvironment serve multiple functions, including homing and lodgement of HSC to the bone marrow during ontogeny or following transplantation, and participation in the direct regulation of their proliferation and differentiation.

The extracellular matrix (ECM) is the major component of connective tissue which provides structural integrity, and promotes cell migration and differentiation. As part of these functions, extracellular matrix molecules such as fibroncetin, collagen, laminin, fibrinogen, and tenascin have been shown to support adhesion of cells in vitro. This adhesive interaction is critical for a number of biological processes including hemostasis, thrombosis, wound healing, tumor metastasis, immunity and inflammation.

A class of receptors involved with mediation of adhesive interaction with extracellular matrix molecules are the integrins, which consist of heterodimeric complexes of non-covalently associated alpha and beta subunits. A common β subunit combines with unique α subunits to form an adhesion receptor of defined specificity. The β1 subfamily, also known as the VLA family (Very Late Activation Antigens), binds to ECM molecules such as FN, collagen and laminin. For reviews, see, Hynes, Cell 48:549 (1987); Hemler, Annu. Rev. Immunol. 8:365 (1990).

Bone marrow transplantation is a useful treatment for a variety of hematological, autoimmune and malignant diseases, where there is a need to replenish hematopoietic cells of the bone marrow (via hematopoiesis) that have been depleted by treatments such as chemotherapy and radiotherapy. Current bone marrow transplantation therapies include the use of hematopoietic cells obtained from umbilical cord blood or from peripheral blood (either unmobilized or mobilized with agents such as G-CSF), as well as directly from the bone marrow.

A limitation in bone marrow transplantation is obtaining enough stem cells to restore hematopoiesis. Current therapies may include the ex vivo manipulation of hematopoietic cells to expand primitive stem cells to a population suitable for transplantation. Moreover, whilst there is rapid regeneration to normal pre-transplantation levels in the number of hematopoietic progenitors and mature end cells following bone marrow transplantation, HSC numbers recover to only 5-10% of normal levels. The available methodologies do not adequately address ex vivo HSC manipulation, and thus the cell populations used in clinical applications are limited by the number of cells that are able to be isolated from the donor. For example, due to the limited number of multipotential HSC in umbilical cord blood, cells from this source can only be used for transplantation in younger patients, and excludes the adult population in need of HSC transplantation therapies.

In addition to issues impacting upon therapeutic uses, there exists the problem of obtaining sufficient numbers of HSC for clinical studies, drug development, or research purposes. An understanding of HSC activity and behaviour is tremendously important in improving the efficacy of therapies, and in determining the toxicity of various therapeutics. Isolation of normally occurring populations of stem or progenitor cells in adult tissues has been technically difficult and costly, due, in part, to the limited quantity of stem or progenitor cells found in blood or tissue, and the significant discomfort involved in obtaining bone marrow aspirates. In general, harvesting of stem or progenitor cells from alternative sources in adequate amounts for therapeutic and research purposes is generally laborious, the sources are limited due to the nature of the harvesting procedures, and the yield is low.

There is therefore a need to provide a method for isolating a cell population enriched in HSCs.

SUMMARY OF THE INVENTION

Accordingly, in a first aspect, the present invention provides a method for selecting HSCs comprising:
  (a) providing a starting population of cells comprising HSCs;
  (b) selecting HSCs within the population by providing an agent which binds to α9β1 on the cell surface of the HSCs; and
  (c) separating HSCs from the starting population of cells by virtue of the binding of the agent.

The binding agent is selective for α9β1 integrin present on HSCs and is preferably selected from the group consisting of SCF, Flt-3, α9β1 antibodies, VCAM1, tenascin C, osteopontin and thrombopoietin, and a ligand which binds α9β1 integrin on the cell surface of HSCs. In a preferred embodiment, the ligand is an antibody.

In a second aspect, there is provided a method for producing a self-renewable population of HSCs comprising:
(a) providing a starting population of cells enriched in HSCs;
(b) culturing HSCs in the presence of an agent which binds to α9β1 integrin present on the cell surface of HSCs wherein the agent inhibits differentiation of the self-renewable HSCs; and
(c) harvesting said population of self-renewable HSCs.

In a preferred embodiment, the agent according to the second aspect is also selected from the group consisting of SCF, Flt-3, α9β1 antibodies, VCAM1, tenascin C, osteopontin and thrombopoietin.

In another preferred embodiment, the agent is immobilized onto a surface. The surface preferably includes the outer layer of a culture device, bead or column, or the surface of a bioreactor.

In yet another preferred embodiment, the method according to the first and second aspects of the invention further comprises the step of activating α9β1 on the cell surface of the HSCs.

In yet another preferred embodiment, the method according to the first and second aspects of the invention further comprises the step of selecting HSCs with activated α9β1 from the population of HSCs.

In a third aspect, the present invention provides an HSC population separated or harvested according to the method defined in the first or second aspects of the invention.

In a fourth aspect, the present invention provides a method for producing a population of lineage committed cells comprising:
(a) providing a starting population of cells enriched in HSCs;
(b) culturing HSCs in the presence of an agent which inhibits or prevents binding to α9β1 integrin present on the cell surface of HSCs, wherein said inhibition increases overall proliferation and differentiation of HSCs to produce lineage committed cells; and
(c) harvesting said lineage committed cells.

In a fifth aspect, the present invention provides a population of lineage committed cells produced according to the method of the fourth aspect of the invention.

BRIEF DESCRIPTION OF THE DRAWINGS

So that the manner in which the above recited features, advantages and objects of the present invention are attained and can be understood in detail, a more particular description of the invention, briefly summarized above, may he had by reference to the embodiments that are illustrated in the appended drawings. It is to be noted, however, that the appended drawings illustrate only certain embodiments of this invention and are therefore not to be considered limiting of its scope, for the present invention may admit to other equally effective embodiments.

DETAILED DESCRIPTION OF THE INVENTION

Figure 1:
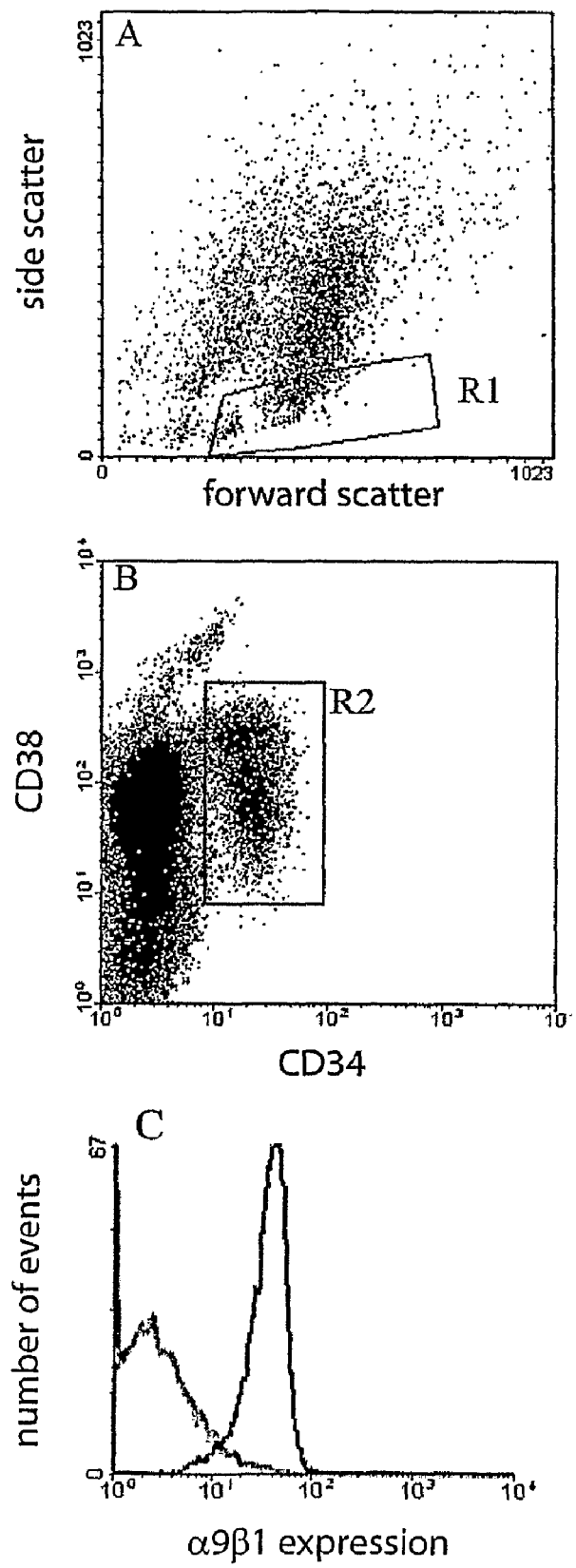
FIG. 1 Primitive human HSC express α9β1—expression of α9β1 by CD34$^+$ cells, shown using antibody labelling and flow cytometry. (A) primitive cells gated on the basis of their forward and side scatter profile (R1) arc (B) analysed for their expression of CD34 and CD38 (R2) and (C) their α9β1 expression (black line) compared to the isotype control (grey line). Representative of aphaeresis product, cord blood (CB) and normal human bone marrow.

Before the present devices, cells and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a factor" refers to one or mixtures of factors, and reference to "the method of production" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention. For example, additional description of apparatus, methods, cell populations and appropriate factors that could be employed for the methods of expansion and differentiation described herein include those described in U.S. Pat Nos.

5,399,493; 5,472,867; 5,635,386; 5,635,388; 5,640,043; 5,674,750; 5,925,567; 6,403,559; 6,455,306; 6,258,597; and 6,280,718.

Generally, conventional methods of cell culture, stem cell biology, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol NO. I, Cold Spring Harbor Laboratory (1998); and Harlow and Lane, Antibodies: A Laboratory Manual, Cold Spring Harbor Laboratory; (1988).

Although the present invention is described primarily with reference to HSC, it is also envisioned that α9β1 and its cell surface interactions may play a role in the regulation of other somatic stem cell populations (including known stem cells such as mesenchymal stem cells or other yet unidentified stem cells) that are involved in lodgement in a microenvironmental niche. The invention is intended to cover α9β1 modulation in these stem cell populations as well as in HSC.

Definitions

The term "antibody" stands for an immunoglobulin protein which is capable of binding an antigen. Antibody as used herein is meant to include the entire antibody as well as any antibody fragments (e.g. F(ab', Fab, Fy) capable of binding the epitope, antigen or antigenic fragment of interest. Preferred antibodies for use in the invention are immunoreactive or immunospecific for and therefore preferentially bind to α9β1. Antibodies for α9β1 are preferably immunospecific—e.g., not substantially cross-reactive with related materials. The term "antibody" encompasses all types of antibodies, e.g. polyclonal, monoclonal, and those produced by the phage display methodology. Particularly preferred antibodies of the invention are antibodies which have a relatively high degree of affinity for the target antigen.

The term "blood cells" is intended to includes erythrocytes (red blood cells), reticulocytes, megakaryocytes, eosinophils, neutrophils, basophils, platelets, monocytes, macrophages, granulocytes and cells of the lymphoid lineage. For the purpose of transfusion of mature cell populations into patients, erythrocytes, granulocytes and platelets are particularly valuable.

The terms "Hematopoietic stem cell", "HSC" and the like are used herein to mean a stem cell having (1) the ability to give rise to progeny in all defined hematopoietic lineages, and (2) stem cells capable of fully reconstituting a seriously immunocompromised host in all blood cell types and their progeny, including the multipotential hematopoietic stem cell, by self-renewal. A multipotential hematopoietic stem cell may be identified by expression of cell surface markers such as $CD34^+$, ACE, CD133 and/or Thy-1. In the context of the present invention, the term HSC is also intended to encompass the population of primitive hematopoietic progenitor cells (HPC).

The term "multipotential" as used herein refers to the ability to produce any cell of the hematopoietic lineage.

the term "pharmacophore" is used herein in an unconventional manner. Although the term conventionally means a geometric and/or chemical description of a class or collection of compounds, as used here the term means a compound that has a specific biochemical activity which activity is obtained by the 3-dimensional physical shape of the compound and the electrochemical properties of the atoms making up the compound. Thus, as used here the term "pharmacophore" is a compound and not a description of a collection of compounds which have defined characteristics. Specifically, a "pharmacophore" is a compound with those characteristics. More specifically, pharmacophores of the invention may, for example, mimic or inhibit α9β1 ligand activity by interaction with an epitope of α9β1 to which a known or identified α9β1 ligand binds. Thus, a pharmacophore of the invention has a shape (i.e., the geometric specifications) and electrochemical characteristics that substantially mimic ligands that bind and lead to activation/modulation of α9β1 or α9β1 binding. The term pharmacophore covers peptides, peptide analogs and small molecules.

The term "preferentially binds" as used herein means high avidity and/or high affinity binding of an antibody to a specific polypeptide e.g., epitope of a protein, e.g., the α9β1 heterodimer or the α9 subunit. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as α9β1 so that by adjusting binding conditions the antibody binds almost exclusively to an epitope site or fragments of a desired protein such as an epitope fragment exposed by denaturing of α9β1 and not exposed on native α9β1.

The Invention

The invention is based on the discovery that α9β1 is a key functional protein for the maintenance of HSC within the HSC microenvironmental niche. The present applicant has found that modulation of α9β1 integrin binding on HSCs can be exploited to provide either a cultured population of self-renewable HSC, or mature lineage committed cells for various applications.

The identification of HSCs expressing α9β1 (i.e., α9β1+ HSCs) serves to facilitate the development of improved methodology for the purification and characterization of HSCs for transplantation purposes.

The methods of the invention include obtaining a population of cells from human hematopoietic tissue. From the cells obtained from the hematopoietic tissue, cells expressing α9β1+ on the surface of the cells are then isolated. In one embodiment, the α9β1+HSCs are isolated using a known ligand, e.g., tenascin C or the cleaved form of osteopontin. However, the present invention should not be construed to be limited to isolation of α9β1+cells using any particular antibody. Rather, the present invention encompasses using any molecule (including an antibody) which specifically binds α9β1 to isolate α9β1+cells including polyclonal antibody.

Accordingly, in a first aspect, the present invention provides a method for selecting HSCs comprising:
 (a) providing a starting population of cells comprising HSCs;
 (b) selecting HSCs within the population by providing an agent which binds to α9β1 on the cell surface of the HSCs; and
 (c) separating HSCs from the starting population of cells by virtue of the binding of the agent.

Preferably, the agent which binds to α9β1 integrin is selected from the group consisting of an α9β1 integrin ligand (such as the cleaved form of Opn, VCAM1, tenascin C), agonists or mimetics of α9β1 integrin ligand which are capable of binding to α9β1 integrin, and chemical analogs of the α9β1 integrin ligand. More preferably, the agent is an antibody or functional fragment thereof which binds to α9β1 integrin present on HSCs.

An important element of this invention is that the binding to α9β1 on HSC can be used to provide a cultured population of HSC that are self-renewable over a span of time, preferably at least one month, more preferably three months, and even more preferably at least six months.

Accordingly, in a second aspect the present invention provides a method for producing a self-renewable population of HSCs comprising:
 (a) Providing a starting population of cells enriched in HSCs;
 (b) culturing HSCs in the presence of an agent which binds to α9β1 integrin present on the cell surface of HSCs wherein the agent inhibits differentiation of the self-renewable HSCs; and
 (c) harvesting said population of self-renewable HSCs.

Preferably, the agent according to the second aspect of the invention is selected from the group consisting SCF, Flt-3, α9β1 antibodies, VCAM1, tenascin C, osteopontin and thrombopoietin.

In yet another preferred embodiment, the method further comprises the administration of a form of Opn which preferentially binds to α9β1 and can be added as a factor to the culture media or provided as an immobilized form of Opn in a cell culture device to promote Opn binding and artificially recapitulate the HSC stromal-mediated microenvironmental niche for HSC expansion and maintenance of their multipotential state.

Preferably, the starting population of cells enriched in HSCs are selected from the group consisting of mobilised peripheral blood HSCs, bone marrow HSCs which may be of fetal or adult origin, and umbilical cord blood HSCs. Preferably such HSCs are enriched in markers characteristic of human HSCs, in particular the CD34 surface marker or the ACE surface marker.

In a specific embodiment, the invention provides populations of HSC expanded from umbilical cord blood. HSC isolated from umbilical cord blood display certain characteristics that potentially make them superior to cells derived from bone marrow. In particular, umbilical cord blood derived HSC and the progeny derived from cord blood do not appear to be as immunogenic as HSC from bone marrow, and thus show improved clinical outcomes in patients without a perfect HLA match. In addition, umbilical cord blood HSC appear to have increased haemopoietic/proliferative potential as compared to HSC isolated from adult haemopoietic tissues. Currently, the use of such HSC is inhibited by the low numbers of HSC that can be isolated from an umbilical source, which are not sufficient for engraftment in an adult. The possibility of using umbilical cord blood for transplantation in adults opens up the use of this cell source to a much wider patient population, and will allow many people who do not currently have an appropriate HLA matched donor to receive HSC transplantation therapy.

In a preferred embodiment, the agent according to the first and second aspects of the invention may be immobilised onto a surface. In one embodiment, an α9β1 ligand is immobilized to a surface of a culture flask, bead, or other surface (such as the surface of a bioreactor), and HSC are exposed to the immobilizing surface to enhance HSC production and prevent proliferation and differentiation of the HSC progeny. This culture device uses α9β1 ligand binding to promote growth and expansion of the HSC population, maintaining the multipotentiality of both the parent HSC and the multipotential progeny HSC. This includes bioreactor culture devices on which the α9β1 ligand is immobilized on the surface. The surface may also comprise other immobilized molecules that, in conjunction with the α9β1 ligand, artificially recapitulate the HSC stromal-mediated microenvironmental niche. These surfaces may have particular relevance in bioreactors such as the hollow fiber bioreactors, e.g., those described in U.S. Pat. No. 5,763,194. Alternatively, modulation of the binding to α9β1 integrin can be exploited to enhance the proliferation and differentiation of HSCs to produce populations of lineage committed cells.

In a preferred embodiment according to the first and second aspects of the invention, the method further comprises the step of activating α9β1 on the HSCs. Activation of α9β1 integrin may be achieved using a number of methods known in the art such as divalent cations such as $Ca^{21}$, $Mg^{2+}$ and $Mn^{2+}$ (Day et al., (2002) Cell Commun Adhes. 9(4):2005-219; Takamatsu et al., (1998) Cell Commun Adhes. 5(5):349-366; Egger et al., (2003) J Pharmacol. Exp. Ther. 306(3):903-913. Activation of α9β1 integrin may also be achieved by means of an antibody specific interaction (see for example van der den Berg et al., (2001) Eur. J. Immunol 31:276-284; Taooka et al., (1999) The Journal of Cell Biology 145:413-420; Kovach et al., (1992) The Journal of Cell Biology 116:499-509), or a combination of a divalent cation and an antibody (Chigaev et al., (2001) The Journal of Biological Chemistry 276(52): 48670-48678).

In another preferred embodiment according to the first and second aspects, the method further comprises the step of selecting HSCs with activated α9β1 from the population of HSCs.

In a third aspect the invention provides an HSC population separated or harvested according to the method of the first or second aspects of the invention.

In a fourth aspect, the present invention provides a method for producing a population or lineage committed cells comprising:
 (a) providing a starting population of cells enriched in HSCs;
 (b) culturing HSCs in the presence of an agent which inhibits or prevents binding to α9β1 integrin present on the HSCs, wherein said inhibition increases overall proliferation and differentiation of HSCs to produce lineage committed cells; and
 (c) harvesting said lineage committed cells.

This method results in an increased number of cells produced in the hematopoietic lineage, which can subsequently be used in other specific therapeutic applications requiring the introduction of cells from the hematopoietic lineage.

The method may be tailored to provide mature cells of a particular cell lineage such as by the inclusion of specific growth factors which drive lineage determination. For example, differentiation may be driven towards erythrocyte precursors which can be used in the treatment of a subject suffering from anemia.

Preferably, an agent which inhibits or prevents binding to α9β1 integrin is selected from the group consisting of antibodies or functional fragments thereof which prevent binding of α9β1 integrin to any of its relevant ligands. Agents that sequester Opn or other counter-receptor molecules would modulate binding and functional activation of the α9β1 integrin on HSC, and are intended to be included in the present the invention. Similarly, any molecule that mimics Opn in its binding and activation of α9β1 integrin (e.g., an Opn pharmacophore) is encompassed by the present invention.

The method according to this aspect inhibits or prevents ligand binding to α9β1 present on HSC to increase overall proliferation and differentiation of HSC populations, and to produce and isolate more mature cell populations from the hematopoietic lineage. This can be an active inhibition, via binding of a molecule that provides stearic hindrance to prevent binding of the active ligand, or a passive inhibition through providing a culturing environment devoid of any α9β1 ligand. Active inhibition may be direct or indirect, i.e. act directly on the α9β1 molecule, or inhibit the activity of a molecule that binds to α9β1 in the culture environment.

In a fifth aspect, the invention provides a population of a lineage committed cells produced by the method according to the fourth aspect of the invention, for use in transplantation therapy.

In one embodiment, the cell populations are isolated to one specific cell type, e.g., red blood cells. In another embodiment, the cell population may be a heterogeneous population or HSC progeny.

In one specific embodiment of the invention, cell production is undertaken in a bioreactor designed for producing clinically useful quantities of mature cells of the hematopoietic lineage. Such a system would require the decreasing binding of α9β1 on the HSC population to promote increased proliferation of the HSC into adequate numbers of differentiated cells. In a further embodiment, the selection system is comprised of a sequential system providing cultured HSCs, with an α9β1 ligand initially provided to the cells to promote expansion of the HSC "culture" population, followed by inhibition of α9β1 binding to promote the increased proliferation and differentiation of cells.

These and other objects, advantages and features of the present invention will become apparent to those persons skilled in the art upon reading the details of the structure of the device, formulation of compositions and methods of use, as more fully set forth below.

Expansion of HSC in ex viva Culture: Cell Sources

HSC may be isolated from any known human source of stem cells, including bone marrow, both adult and fetal, mobilized peripheral blood, and umbilical cord blood. Initially, bone marrow cells may be obtained from a source of bone marrow, including ilium (e.g., from the hip bone via the iliac crest), tibia, femora, spine, or other bone cavities. Other sources of stem cells include embryonic yolk sac, fetal liver, and fetal spleen. The HSC sourced for use in the methods of the invention can comprise a heterogeneous population of cells including a combination of multipotential HSC, immunocompetent cells and stromal cells including fibroblast and endothelial cells.

Umbilical cord blood is comparable to bone marrow as a source of hematopoietic stem cells and progenitors (Broxmeyer et al., 1992; Mayani et al., 1993). In contrast to bone marrow, cord blood is more readily available on a regular basis, and does not require the unpleasant issues involved with obtaining bone marrow from a donor.

Methods for mobilizing stem cells into the peripheral blood are known in the art and generally involve treatment with chemotherapeutic drugs, e.g., cytoxan, cyclophospharnide, VP-16, and cytokines such as GM-CSF, G-CSF, SCF, or IL-3, or combinations thereof. Daily leukapheresis samples may be monitored for the presence of $CD34^+$ and/or $Thy-1^+$ cells to determine the peak of stem cell mobilization and, hence, the optimal time for harvesting peripheral blood stem cells.

Enrichment of HSC from Sourced Cells

Binding to α9β1 on HSC provides a novel and potent means of improving various ex vivo manipulations such as ex vivo expansion of stem cells and genetic manipulation of stem cells. The HSC used in such a device preferably are isolated HSC populations, although it is intended that the methods, media and devices of the invention can also be used for ex vivo expansion of HSC in heterogeneous cell populations such as adult human bone marrow or human umbilical cord blood cells.

An example of an enriched human HSC population is a population of cells selected by expression of the $CD34^+$ marker. In long term culture initiating cell (LTCIC) assays, a population enriched in $CD34^+$ cells will typically have an LTCIC frequency in the range of 1/50 to 1/500, more usually in the range of 1/50 to 1/200. Preferably, the HSC population will be more highly enriched for HSC than that provided by a population selected on the basis of $CD34^+$ expression alone. By use of various techniques described more fully below, a highly enriched HSC population may be obtained. A highly enriched HSC population will typically have an LTCIC frequency in the range of 1/5 to 1/100, more usually in the range of 1/10 to 1/50. Preferably, it will have an LTCIC frequency of at least 1/50. Exemplary of a highly enriched HSC population is a population having the $CD34^+ Lin^-$ or $CD34^+ Thy-1^+ Lin^-$ phenotype as described in U.S. Pat. No. 5,061,620 incorporated herein by reference to disclose and describe such cells. A population of this phenotype will typically have an average LTCIC frequency of approximately 1/20 (Murray et al., *Enrichment of Human Hematopoietic Stem Cell Activity in the $CD34^+Thy-1^+Lin$-Subpopulation from Mobilized Peripheral Blood*, Blood, vol. 85, No. 2, pp. 368-378 (1995); Lansdorp et al. (1993) J. Exp. ed. 177:1331). LTCIC frequencies are known to correlate with CAFC frequencies (Reading et al., Proceedings of ISEH Meeting 1994, Abstract, Exp. Hematol., vol. 22:786, 406, (1994).

Another example of an enriched human HSC population is a population of cells selected by expression of cell surface ACE ($ACE^+$ cells). ACE has been identified as an early marker on multipotent cells of the hematopoietic lineage, and is closely but not completely correlated with expression of CD34. Methods for isolation of cells based on this marker are described in WO 03/016916, *Identification and Isolation of Somatic Stem Cells & Uses Thereof*.

Various techniques may be employed to separate the cells by initially removing cells of dedicated lineage ("lineage-committed" cells). Monoclonal antibodies are particularly useful for identifying markers associated with particular cell lineages and/or stages of differentiation. The antibodies may be attached to a solid support to allow for crude separation. The separation techniques employed should maximize the viability of the fraction to be collected.

The use of separation techniques include those based on differences in physical (density gradient centrifugation and counter-flow centrifugal elutriation), cell surface (lectin and antibody affinity), and vital staining properties (mitochondria-binding dye rhodamine 123 and DNA-binding dye Hoechst 33342). Procedures for separation may include magnetic separation, using antibody-coated magnetic beads, affinity chromatography, cytotoxic agents joined to a monoclonal antibody or used in conjunction with a monoclonal antibody, including complement and cytotoxins, and "panning" with antibody attached to a solid matrix or any other convenient technique. Techniques providing accurate separation include flow cytometry which can have varying degrees of sophistication, e.g., a plurality of color channels, low angle and obtuse light scattering detecting channels, impedance channels, etc.

A large proportion of the differentiated cells may be removed by initially using a relatively crude separation, where major cell population lineages of the hematopoietic system, such as lymphocytic and myelomonocytic, are removed, as well as lymphocytic populations, such as megakaryocytic, mast cells, eosinophils and basophils. Usually, at least about 70 to 90 percent of the hematopoietic cells will be removed.

Concomitantly or subsequent to a gross separation providing for positive selection, e.g., using the CD34 marker, a negative selection may be carried out, where antibodies to lineage-specific markers present on dedicated cells are employed. For the most part, these markers include CD2, CD3, CD7, CD8, CD10, CD14, CD15, CD16, CD19, CD20, CD33, CD38, CD71, HLA-DR, and glycophorin A; preferably including at least CD2, CD14, CD15, CD16, CD19 and glycophorin A; and normally including at least CD14 and CD15. As used herein, Lin⁻ refers to a cell population remaining after removal of cells bearing single or combinations of the lineage associated antigens recognised by antibodies directed against CD2, CD3 etc. The hematopoietic cell composition substantially depleted of dedicated cells may be further separated using selection for Thy-1⁺ and/or Rho123[10], whereby a highly enriched HSC population is achieved.

The purified HSC have low side scatter and low to medium forward scatter profiles by FACS analysis. Cytospin preparations show the enriched HSC to have a size between mature lymphoid cells and mature granulocytes. Cells may be selected based on light-scatter properties as well as their expression of various cell surface antigens.

Cells can be initially separated by a coarse separation, followed by a fine separation, with positive selection of a marker associated with HSC and negative selection for markers associated with lineage committed cells. Compositions highly enriched in HSC may be achieved in this manner. The desired stem cells are exemplified by a population with the CD34⁺ Thy-1⁺ Lin phenotype, and are characterized by being able to be maintained in culture for extended periods of time, being capable of selection and transfer to secondary and higher order cultures, and being capable of differentiating into the various lymphocytic and myelomonocytic lineages, particularly B- and T-lymphocytes, monocytes, macrophages, neutrophils, erythrocytes and the like.

Accordingly, the present invention includes a two-step method of obtaining a purified population of human HSCs. The first stop involves the purification of hematopoietic progenitor cells from cells obtained from human hematopoietic tissue using an early marker such as CD34[1]. The first step may be as generally described above, and may include one or more separation techniques. The second step includes further purification of this cell population by an additional separation based on the presence or absence of α9β1.

In the second step, the human hematopoietic progenitor cells isolated previously are selected for the expression of α9β1.

Other methods known in the art for separation of cell subsets or methods to be developed, may also be used to practice the present invention. The purification of α9β1⁺ cells may be modified by using any other reagent or combination of reagents such as any monoclonal antibody or combination of monoclonal antibodies used together with any reagent which specifically bind α9β1.

Pharmacopohore Design and the α9β1-Opn Interface

α9β1 and the cleaved form of Opn forms a complex with a particular molecular interaction, and pharmacophores fitting this geometric and chemical description can be used in the present methods to interfere with the α9β1-Opn interface. The inhibitors can be used to inhibit the interaction of α9β1 in vivo (e.g., in the HSC microenvironmental niche) or ex vivo (e.g., in an expansion culture to influence the cell type predominately available following culture and expansion).

Identifying pharmacophores of the invention requires the identification of small molecules, peptides, and the like that mimics the positive image of the residues that comprise the Ostepontin binding site on the heterodimeric complex of α9β1. A successful compound binds to α9β1, modifying its action, and thereby Opn modulation of the α9β1 molecule.

Assays to Identify Inhibitor Pharmacophores

Candidate molecules as inhibitory pharmacophores can encompass numerous chemical classes, including, but not limited to, peptides and small molecules. Candidate pharmacophores can comprise functional groups necessary for structural interaction with proteins, particularly hydrogen bonding, and typically include at least an amine, carbonyl, hydroxyl or carboxyl group, preferably at least two of the functional chemical groups. The candidate pharmacophores often comprise cyclical carbon or heterocyclic structures and/or aromatic or polyaromatic structures substituted with one or more of the above functional groups. Candidate inhibitor pharmacophores are also found among biomolecules including, but not limited to: polynucleotides, peptides, saccharides, fatty acids, steroids, purines, pyrimidines, derivatives, structural analogs or combinations thereof.

Candidate inhibitor pharmacophores can be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacologically relevant scaffolds may be subjected to directed or random chemical modifications, such as acylation, alkylation, esterification, amidification, etc. to produce structural analogs.

Identification of structural aspects of proteins involved in α9β1-ligand complex formation, can define a tertiary structure to be used in an assay to design pharmacophores that modulate molecules and/or protein:protein interactions in the complex. Specifically, a dataset of compounds (small molecules, peptides, etc) having a particular tertiary structure can be identified using techniques known in the art, such as medicinal chemistry, combinatorial chemistry and molecular modelling, to determine molecules that are likely to bind to the atoms or groups of atoms of a protein involved in the binding of Opn or tenascin C. Optionally, factors such as hydrophobicity and hydrophilicity, placement of the functional residues in a structural motif, and mutations involved in hematopoietic disorders may also be taken into account.

In a preferred embodiment of the assay of the invention, the assay involves (1) matching compounds in a library with the binding site regarding spatial orientation; (2) screening candidate compounds visually using computer generated molecular display software; and (3) experimentally screening actual compounds against α9β1 in the presence of an α9β1 ligand (e.g., tenascin C or cleaved Opn) to determine compounds which inhibit or enhance HSC-related signalling activity through α9β1.

Once the functional residues of the target protein are identified, this portion of the molecule can serves as a template for comparison with known molecules, e.g., in a database such as Available Chemicals Database (ACD, Molecular Design Labs, 1997), or it may be used to design molecules de novo. In one example, the initial group of identified molecules may contain tens or hundreds of thousands or more of different non-peptide organic compounds. A different or supplemental group may contain millions of different peptides which could be produced synthetically in chemical reactions or via bacteria or phage. Large peptide libraries and methods of making such are disclosed in U.S. Pat No. 5,266,684, issued Nov. 30, 1993, and U.S. Pat. No. 5,420,246, issued May 30, 1995, which are incorporated herein by reference. Libraries of non-peptide organic molecules are disclosed in PCT publication WO 96/40202, published Dec. 19, 1996, incorporated herein by reference.

The initial library of molecules is screened via computer generated modeling, e.g., computer models of the compounds are matched against a computer model of the Opn ligand binding site on α9β1 to find molecules which mimic the spatial orientation and basic structure of the Opn epitope. This screening should substantially reduce the number of candidate molecules relative to the initial group.

The screened group is then subjected to further screening visually using a suitable computer program which makes viewable images of the molecules. The resulting candidate molecules are then tested for their ability to inhibit Opn-α9β1 formation.

Culture Methods and Devices for Expansion of HSC Populations

An α9β1 ligand can be added to the media to promote binding to HSC and may act as one component interaction in an artificially recapitulated HSC stromal-mediated microenvironmental niche (one of the multitude of interactions in which HSC participate). The specific HSC expansion media can be used to establish and maintain a multipotential HSC population for various uses. In a specific embodiment, the culture media also contains thrombin to further enhance α9β1 binding on HSC.

Alternatively, an α9β1 ligand can he immobilized to a surface of a culture flask, bead, or other surface of a culture device (such as the surface of a bioreactor), and the HSC exposed to the immobilizing surface. HSC will bind the appropriate ligand in or on the culture device, which will have two major effects: 1) the α9β1 ligand will immobilize the cell on the surface in the culture system and 2) the α9β1 ligand will promote expansion of the multipotential HSC population.

Immobilized α9β1 ligand can be used in conjunction with other immobilized proteins that bind to HSC (such as agents that bind to angiotensin converting enzyme (ACE), CD59, CD34 and/or Thy-1) in either the culture media or alternatively immobilized on the culture device to artificially recapitulate elements of the HSC microenvironmental niche. The immobilized ligand can be used in conjunction with immobilized haemopoietic growth factors specifically, e.g., SCF, Flt3-L Upon cell division of the HSC, the multipotential HSC progeny produced will also bind to α9β1 ligand, thus expanding the number of immobilized cells in the culture system.

Cells not expressing α9β1 will not become immobilized, and thus can be removed from the culture system. For example, where α9β1 ligand is immobilized in a flow through bioreactor, any HSC progeny not binding to α9β1 ligand would be separated from the HSC culture during the flow through of the culture media. Thus, differentiating cells lacking the α9β1 can be eluted or otherwise separated from the bound cells. This will allow not only expansion of the primordial HSC population, but will also promote greater homogeneity of this population through a de facto α9β1 ligand selection process.

In one embodiment, the invention provides an HSC production device, i.e. a culture device for ex vivo expansion of multipotential HSC populations. This production device will deliver α9β1 ligand to an HSC population in either immobilized form or via media introduced to the culture device. Preferably, the HSC population has been isolated from its starting material using one or a combination of cell surface markers, e.g., CD34 or angiotensin converting enzyme (ACE), prior to introduction of the HSC to the culture device. It is envisaged, however, that the HSC may be present in a heterogeneous cell population prior to introduction to the device, with the device having the ability to isolate the relevant HSC population based on other immobilized molecules that preferentially bind to the HSCs. Such heterogeneous populations include HSC present in adult human bone marrow or human umbilical cord blood cells.

The bioreactors that may be used in the present invention provide a culture process that can deliver medium and oxygenation at controlled concentrations and rates that mimic nutrient concentrations and rates in vivo. Bioreactors have been available commercially for many years and employ a variety of types of culture technologies. Once operational, bioreactors provide automatically regulated medium flow, oxygen delivery, and temperature and pH controls, and they generally allow for production of large numbers of cells. The most sophisticated bioreactors allow for set-up, growth, selection and harvest procedures that involve minimal manual labor requirements and open processing steps. Such bioreactors optimally are designed for use with a homogeneous cell mixture such as the bound HSC populations contemplated by the present invention.

Of the different bioreactors used for mammalian cell culture, many have been designed to allow for the production of high density cultures of a single cell type and as such find use in the present invention. Typical application of these high density systems is to produce, as the end-product, a conditioned medium produced by the cells. This is the case, for example, with hybridoma production of monoclonal antibodies and with packaging cell lines for viral vector production. One aspect of the invention is thus the production of conditioned HSC media where the end-product is the HSC conditioned media.

Suitable bioreactors for use in the present invention include but are not limited to those described in U.S. Pat. No. 5,763, 194 to Slowiaczek, et al., particularly for use as the culture bioreactor; and those described in U.S. Pat. Nos. 5,985,653 and 6,238,908 to Armstrong, et al., U.S. Pat. No. 5,512,480 to Sandstrom, et al., and U.S. Pat. Nos. 5,459,069, 5,763,266, 5,888,807 and 5,688,687 to Palsson, et al., and U.S. Pat. No. 5,763,194 to Slowiaczek et al., particularly for use as the proliferation and differentiation bioreactors of the present invention.

Attachment of α9β1 Ligand to a Culture Device Surface

Non-covalent attachment is known in the art and includes, but is not limited to, attachment via a divalent ion bridge, e.g., a Ca++, Mg++ or Mn++ bridge; attachment via absorption of α9β1 ligand or a fragment thereof to the material; attachment via plasma spraying or coat drying of a polyamine, e.g., polylysine, polyarginine, spermine, spermidine or cadaverin, onto the material; attachment via a second polypeptide, e.g., fibronectin or collagen, coated onto the material; or attachment via a bifunctional crosslinker, e.g., N-Hydroxysulfosuccinimidyl-4-azidosalicylic acid (Sulfo-NHS-ASA), Sulfosuccinimidyl(4-azidosalicylamido)hexanoate (Sulfo-NHS-LC-ASA), N-γ-maleimidobutyryloxysuccinimide ester (GMBS), N-γ-maleimidobutyryloxysulfosuccinimide ester (Sulfo-GMBS), 4-Succinimidyloxycarbonyl-methyl-α-(2-pyridyldithio)-toluene (SMPT), Sulfosuccinimidyl 6[α-methyl-α(2-pyridyldithio)toluamido]hexanoate (Sulfo-LC-SMPT), N-Succinimidyl-3-(2-pyridyldithio)propionate (SPDP), Succinimidyl 6-[3-(2-pyridyldithio)propionamide] hexanoate (LC-SPDP), Sulfosuccinimidyl 6-[3-(2-pyridyldithio)propionamido]hexanoate (Sulfo-LC-SPDP), Succinimidyl 4-(N-maleimidomethyl)cyclohexane-1-carboxylate (SMCC), Sulfosuccinimidyl 4-(N-maleimidomethyl)cyclohexane-1-carboxylate (Sulfo-SMCC), m-Maleimidobenzoyl-N-hydroxysuccinimide ester (MBS), m-Maleimidobenzoyl-N-hydroxysulfosuccinimide ester (Sulfo MBS), N-Succinimidy(4-iodoacetyl)amino benzoate (SIAB), Sulfosuccinimidyl(4-iodoacetyl)amino benzoate (Sulfo-SIAB), Succinimidyl 4-(p-maleimidophenyl)butyrate (SMPB), Sulfosuccinimidyl 4-(p-maleimidophenyl)butyrate (Sulfo-SMPB), or Azidobenzoyl hydazide (ABH), to the material. In other embodiments α9β1 ligand or an active fragment of α9β1 ligand is attached to the material via an electrostatic interaction.

Alternatively, the α9β1 ligand can be attached to a surface via non-covalent attachment, as described above, further including a glycosaminoglycan. Based on the interaction between α9β1 ligand, CD44 and hyaluronic acid, the preferred glycosaminoglycan is hyaluronic acid, and more preferably hyaluronic acid greater than a disaccharide. In one embodiment the hyaluronic acid has a molecular weight range of less than 100 kDa, more preferably between about 20 to about 100 kDa, e.g., between about 50-100, 70-100, or 30-80 kDa.

Culturing Media and Devices for Promoting Cell Proliferation and Differentiation The bioreactor and culture conditions used to proliferate the more differentiated cells will vary depending on the ultimate mature cell product desired. Several "classic" bioreactors are known in the art and may be used, including bioreactor as as described in U.S. Pat. Nos. 5,985,653 and 6,238,908 to Armstrong, et al., U.S. Pat. No. 5,512,480 to Sandstrom, et al., and U.S. Pat. Nos. 5,459,069, 5,763,266, 5,888,807 and 5,688,687 to Palsson, et al.

The differentiated cell populations following α9β1 ligand-blocking proliferation may be transit amplifying (TA) cells, or other uncommitted common precursors of mature, completely differentiated blood cells. TA cells can be proliferated in a first step followed by further proliferation to the desired blood cell. The further differentiated cells can be distinguished from primordial cells by cell surface markers, and the desired cell type can be identified or isolated based on such markers. For example, LIN⁻ HSC lack several markers associated with lineage committed cells. Lineage committed markers include those associated with T cells (such as CD2, 3, 4 and 8), B cells (such as CD10, 19 and 20), myeloid cells (such as CD14, 15, 16 and 33), natural killer ("NK") cells (such as CD2, 16 and 56), RBC (such as glycophorin A), megakaryocytes (CD41), or other markers such as CD38, CD71, and HLA-DR. Populations highly enriched in HSC and methods for obtaining them are described in PCT/US94/09760; PCT/US94/08574 and PCT/US94/10501.

Other culture conditions, such as medium components, $O_2$ concentration, differentiation factors, pH, temperature, etc., as well as the bioreactor employed, will vary depending on the desired cell population to be differentiated and the desired differentiated cell type, but will differ primarily in the cytokine(s) used to supplement the differentiation medium. The maturation process into a specific lineage can be modulated by a complex network of regulatory factors. Such factors include cytokines that are used at a concentration from about 0.1 ng/ml to about 500 ng/mL, more usually 10 ng/mL to 100 ng/mL. Suitable cytokines include but are not limited to c-kit ligand (KL) (also called steel factor (Stl), mast cell growth factor (MGF), stem cell growth factor (SC-GF), and stem cell factor (SCF)), macrophage colony stimulating factor (M-CSF), IL-1α, IL-2, IL-3, IL-4, IL-5, IL-6, IL-11, G-CSF, GM-CSF, MIP-1, LIF, c-mpl ligand/thrombopoietin, erythropoietin, and flk2/flk3 ligand. The differentiation culture conditions will include at least two of the cytokines listed above, and may include several.

For example, if red blood cells are the desired mature blood product, at least erythropoietin will be added to the culture medium, and preferably SC-GF, IL-1, IL-3, IL-6 will be added to the culture medium, possibly with erythropoietin added later as a terminal differentiating factor. If platelets are the desired mature blood product, preferably SC-GF, IL-1, IL-3, SCF, TPO, GM-CSF and/or IL-11 will be added to the culture medium. For example, the path for the differentiation of T cells requires that the cell population be differentiated with IL-1 and IL-6, followed by differentiation with IL-1, IL-2 and IL-7, followed by differentiation with IL-2 and IL-4.

Alternatively to directing differentiation to a single cell type, the final product could be a mixed population and the cells could be separated using current cell separation techniques and procedures.

Inhibition of α9β1 ligand binding to HSC also has utility in providing cell populations for applications such as research, screening for compounds or agents that alter HSC function or viability, toxicity testing of pharmaceutical agents and the like. Providing an HSC starting culture, and selectively enhancing proliferation of more mature cell types via inhibition of α9β1 ligand binding to HSC, will allow not only an increase in HSC proliferation but specifically promote production of the more differentiated progeny.

Thus, in one embodiment, the invention provides media for HSC proliferation and differentiation containing one or more agents that inhibit α9β1 ligand. The inhibition of α9β1 ligand may be provided either in a single culture system, or in sequential culture systems (i.e., sequential bioreactors with different media). This is particularly useful if the culture system involves sequential culture conditions.

For example, to maximize the number of differentiated progeny produced, it may be desirable to first expand the HSC population via α9β1 ligand binding, (with α9β1 ligand provided immobilized in the culture setting or provided to the culture setting via media containing α9β1 ligand) followed by inhibition of α9β1 ligand to accelerate proliferation and differentiation of the more mature hematopoietic progeny.

Although a single α9β1 ligand inhibitor may be used in the methods of the invention, in one embodiment it would be preferable to use multiple agents, (e.g., multiple antibodies to various α9β1 ligand epitopes) to ensure the inhibition of α9β1 ligand in the culture system and/or media, especially as α9β1 ligand is known to bind to multiple cell adhesion molecules. Antibodies to α9β1 which display agonist activity, and preferably activating monoclonal antibodies can be used in specific aspects of the present invention. The α9β1 ligand inhibitory molecules contained in the media can be replenished by media perfusion. Alternatively, the α9β1 ligand inhibitory molecules may be added separately, without media perfusion, as a concentrated solution through separate means in the culture system (e.g., into inlet ports in a bioreactor). When a binding agent is added without perfusion, it will typically be added as a 10-100× solution in an amount equal to one-tenth to 1/100 of the volume in the culture system, although it will of course depend on the actual affinity of the particular agent or agents to α9β1 ligand.

In an exemplary embodiment, α9β1 ligand binding and/or inhibition is used in the production of blood cells. Once differentiated, selection for the desired blood cell type can be performed by looking for cell surface markers. For examples T cells are known to have the markers CD2, 3, 4 and 8; B cells have CD10, 19 and 20; myeloid cells are positive for CD14, 15, 16 and 33; natural killer ("NK") cells are positive for CD2, 16 and 56; red blood cells are positive for glycophorin A; megakaryocytes have CD41; and mast cells, eosinophils and basophils are known to have markers such as CD38, CD71, and HLA-DR.

Once produced, the blood cells may also be preserved for future use. Preservation of blood cells can be accomplished by any method known in the art. For example, general protocols for the preservation and cryopreservation of biological products such as blood cells are disclosed in U.S. Pat. Nos. 6,194,136 and 5,364,756 to Livesey, et al.; and U.S. Pat. No. 6,602,718 to Augello, et al. In addition, solutions and methods for the preservation of red blood cells are disclosed in U.S. Pat. No. 4,386,069 to Estep, and preservation of platelets is disclosed in U.S. Pat. Nos. 5,622,867, 5,919,614, and 6,211,669 to Livesey, et al., as well as recent reports regarding new methods from HyperBaric Systems, Inc. and Human Biosystems, Inc.

It is envisioned that the cells produced using the methods of the invention can be used therapeutically to treat various blood disorders. The use of α9β1 ligand in the culturing system will promote the expansion of the HSC into therapeutically relevant amounts of cells.

In a specific embodiment, the cells produced are erythrocytes (red blood cells). The major function of red blood cells is to transport oxygen to tissues of the body. Minor functions include the transportation of nutrients, intercellular messages and cytokines, and the absorption of cellular metabolites. Anemia, or a loss of red blood cells or red blood cell capacity, can be grossly defined as a reduction in the ability of blood to transport oxygen and may be acute or chronic. Chronic blood loss may be caused by extrinsic red blood cell abnormalities, intrinsic abnormalities or impaired production of red blood cells. Extrinsic or extra-corpuscular abnormalities include antibody-mediated disorders such as transfusion reactions and erythroblastosis, mechanical trauma to red cells such as micro-angiopathic hemolytic anemias, thrombotic thrombocytopenic purpura and disseminated intravascular coagulation. In addition, infections by parasites such as Plasmodium, chemical injuries from, for example, lead poisoning, and sequestration in the mononuclear system such as by hypersplenism can provoke red blood cell disorders.

Some of the more common diseases of red cell production include aplastic anemia, hypoplastic anemia, pure red cell aplasia and anemia associated with renal failure or endocrine disorders. Disturbances of the proliferation and differentiation of erythroblasts include defects in DNA synthesis such as impaired utilization of cyanocobalamin or folic acid and the megaloblastic anemias, defects in heme or globin synthesis, and anemias of unknown origins such as sideroblastic anemia, anemia associated with chronic infections such as malaria, trypanosomiasis, HIV, hepatitis virus or other viruses, and myelophthisic anemias caused by marrow deficiencies.

Monoclonal Antibodies to α9β1

In a specific embodiment the pharmaceutical is comprised of a monoclonal antibody that selectively binds to α9β1, either to a single subunit (e.g., an antibody specific to α9) or to the heterodimer. The antibody for human therapeutic use may be humanized or derived initially from a human source (e.g., phage display).

One method for selecting an antibody which preferentially binds to α9β1 is by using a hybridoma which produces a murine monoclonal antibody which preferentially binds to α9β1. These hybridomas provide a reliable source of well-characterized reagents for the construction of antibodies and are particularly useful when their epitope reactivity and affinity has been previously characterized. Another source for such construction includes the use of human monoclonal antibody producing cell lines. (Marasco, W. A., et al., Proc Natl Acad Sci USA, 90:7889-7893 (1993); Chen, S. Y., et al., Proc Natl Acad Sci USA 91:5932-5936 (1994)). Another example includes the use of antibody phage display technology to construct new antibodies against different epitopes on a target molecule. (Burton, D. R., et al., Proc Natl Acad Sci USA 88:10134-10137 (1991); Hoogenboom H. R. et al., Immunol Rev 130:41-68 (1992); Winter G., et al., Annu Rev Immunol 12:433-455 (1994); Marks, J. D., et al., J Biol Chem 267: 16007-16010 (1992); Nissim, A., et al., EMBO J 13:692-698 (1994); Vaughan T. J., et al., Nature Bio 14:309-314 (1996); Marks C., et al., New Eng J Med 335:730-733 (1996)). For example, very large naive human sFv libraries have been and can be created to offer a large source or rearranged antibody genes against a plethora of target molecules. Smaller libraries can be constructed from individuals with autoimmune (Portolano S., et al., J Immunol 151:2839-2851 (1993); Barbas S. M., et al., Proc Natl Acad Sci USA 92:2529-2533 (1995)) or infectious diseases (Barbas C. F, et al., Proc Natl Acad Sci USA 89:9339-9343 (1992); Zebedee S. L., et al., Proc Natl Acad Sci USA 89:3175-3179) (1992)) in order to isolate disease specific antibodies.

Other sources include transgenic mice that contain a human immunoglobulin locus instead of the corresponding mouse locus as well as stable hybridomas that secrete human antigen-specific antibodies, (Lonberg, N., et al., Nature 368: 856-859 (1994); Green, L. L., et al., Nat Genet 7:13-21 (1994)). Such transgenic animals provide another source of human antibody genes through either conventional hybridoma technology or in combination with phage display technology. In vitro procedures to manipulate the affinity and fine specificity of the antigen binding site have been reported including repertoire cloning (Clackson, T., et. al., Nature 352:624-628 (1991); Marks, J. D., et al., J Mol Biol 222:581-597 (1991); Griffiths, A. D., et al., EMBO J 12:725-734 (1993)), in vitro affinity maturation (Marks, J. D., et al., Biotech 10:779-783 (1992); Gram H., et al., Proc Natl Acad Sci USA 89:3576-3580 (1992)), semi-synthetic libraries (Hoogenboom, H. R., supra; Barbas, C. F., supra; Akamatsu, Y., et al., J Immunol 151:4631-4659 (1993)) and guided selection (Jespers, L. S., et al., Bio Tech 12:899-903 (1994)). Starting materials for these recombinant DNA based strategies include RNA from mouse spleens (Clackson, T., supra) and human peripheral blood lymphocytes (Portolano, S., et al., supra; Barbas, C. F., et al., supra; Marks, J. D., et al., supra; Barbas, C. F., et al:, Proc Natl Acad Sci USA 88: 7978-7982

(1991)) and lymphoid organs and bone marrow from HIV-1-infected donors (Burton, D. R., et al., supra; Barbas, C. F., et al., Proc Natl Acad Sci USA 89:9339-9343 (1992)).

Thus, one can readily screen an antibody to insure that it has a sufficient binding affinity for the α9β1. The binding affinity ($K_d$) should preferably be at least about $10^{-7}$ 1/mol, more preferably at least about $10^{-8}$ 1/mol.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrated and not restrictive.

Efforts have been made to ensure accuracy with respect to numbers used (e.g. amounts, temperature, etc.) but some experimental errors and deviations should be accounted for. Unless indicated otherwise, pairs are parts by weight, molecular weight is weight average molecular weight, temperature is in degrees centigrade, and pressure is at or near atmospheric.

Example 1

Expression of α9β1 by HSCs

Cord blood was collected into sodium citrate and held at room temperature (RT) until processed. Low density BM cells were isolated from CD by discontinuous density centrifugation using Ficoll-Hypaque (1.077 g/ml, Pharmacia Biotech, Sweden). A variation of the Dynal bead method for clinical scale selection of cells using the Isolex 300i was used for isolation of CD34[1] cells. CB mononuclear cells were incubated with anti-CD34, washed and exposed to Dynal anti-mouse IgG beads to rosette CD34$^+$ cells. CD34$^+$ cells were captured and incubated with peptide release agent to isolate CD34$^+$ cells. Cells were immunolabelled with a cocktail of CD34-FITC and CD38-PE (Becton Dickinson) for subsequent isolation of CD34$^+$, CD34$^+$CD38 and CD34$^1$CD38$^+$ cells by FACS. α9β1 expression was analysed by co-labelling using an anti-mouse biotin secondary antibody and a strep-avidin Red670 tertiary antibody. Immunolabelled cells were sorted on a FACStar$^{PLUS}$ (Becton Dickinson).

FIG. 1A shows the gating of the cells on the basis of their forward and side scatter profile. FIG. 1B shows the expression of CD34 and CD38 and FIG. 1C shows the expression of α9β1 labelled with Red670 was analysed for the population of cells (R2) gated in FIG. 1B.

Figure 2:
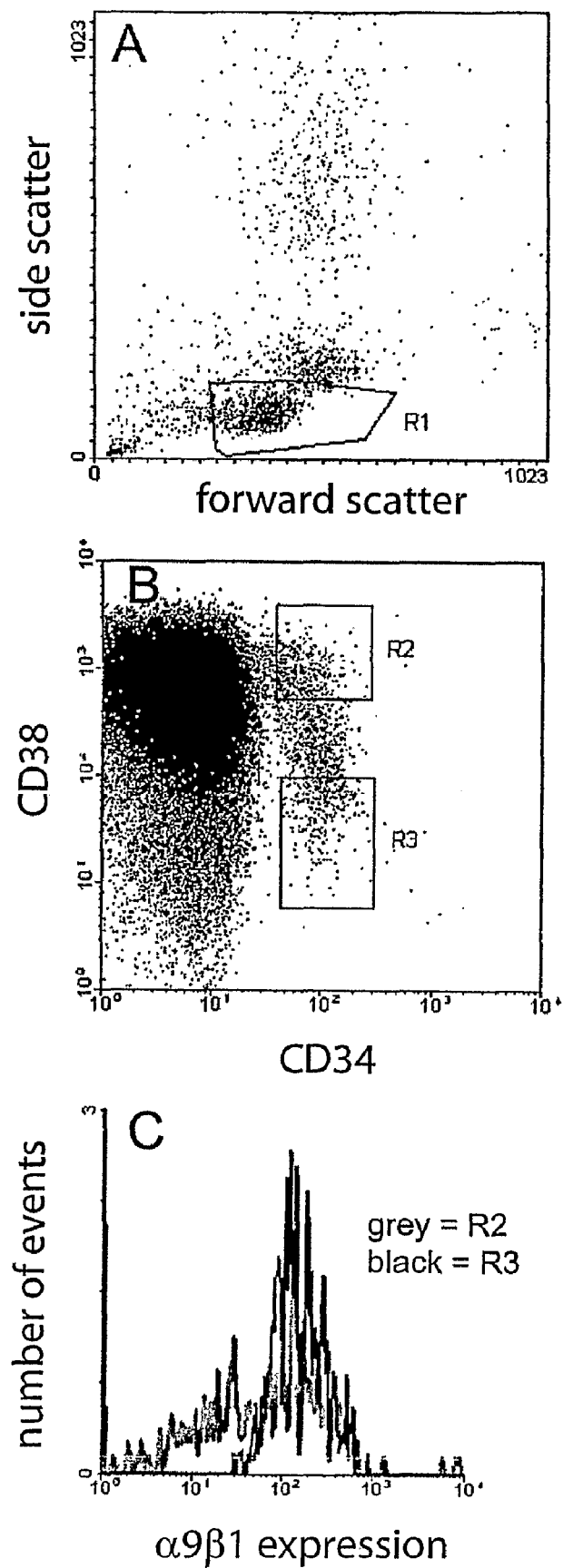
FIG. 2 α9β1 expression is greatest on primitive human HSC—expression of α9β1 by CD34$^+$ cells, shown using antibody labelling and flow cytometry. (A) primitive cells gated on the basis of their forward and side scatter profile (R1) are (B) analysed for their expression of CD34 and CD38 (R2) and (C) their α9β1 expression was greatest on CD34$^+$CD38$^-$ (black line) compared to CD34$^+$CD38$^+$ cells (grey line). Representative of aphaeresis product, CB and normal human bone marrow.

The results show that human HSC's express α9β1. Expression of α9β1 by CD34$^+$ cells was shown using antibody labelling and flow cytometry. FIG. 2A shows primitive cells gated on the basis of their forward and side scatter profile (R1) and FIG. 2B analysed for their expression of CD34 and CD38 (R2). FIG. 2C shows their α9β1 expression was greatest on CD34$^+$CD38$^-$ (black line) compared to CD34$^1$CD38$^+$ cells (grey line). Representative of aphaeresis product, CB and normal human bone marrow.

The results show that α9β1 expression is greatest on primitive human HSC.

Example 2

α9β1 Antibody Significantly Inhibits Human Hematopoiesis in vitro but not as Extensively as Thrombin-Cleaved Opn Human cord blood cells were sorted by FACS and plated into cell culture wells (300 cells/well) in the presence of Cellgro supplemented with 6 growth factors G-CSF, CSF, FL-T3 ligand, (FLT3-L), MGDF (all 100 ng/ml), IL-6 and IL-3 (both 10 ng/ml). In addition, α9β1 antibody (Chemicon), thrombin-cleaved bovine Opn (R & D Systems, Minneapolis, Minn., USA), or Opn inhibiting peptide [SV-VYGLR-NH$_2$] (Auspep) (SEQ ID NO:1) were added. All cells were cultured at 37° C. in 5% $O_2$, 10% $CO_2$ and 85% $N_2$. Cells were grown for 6 days prior to counting.

Figure 3:
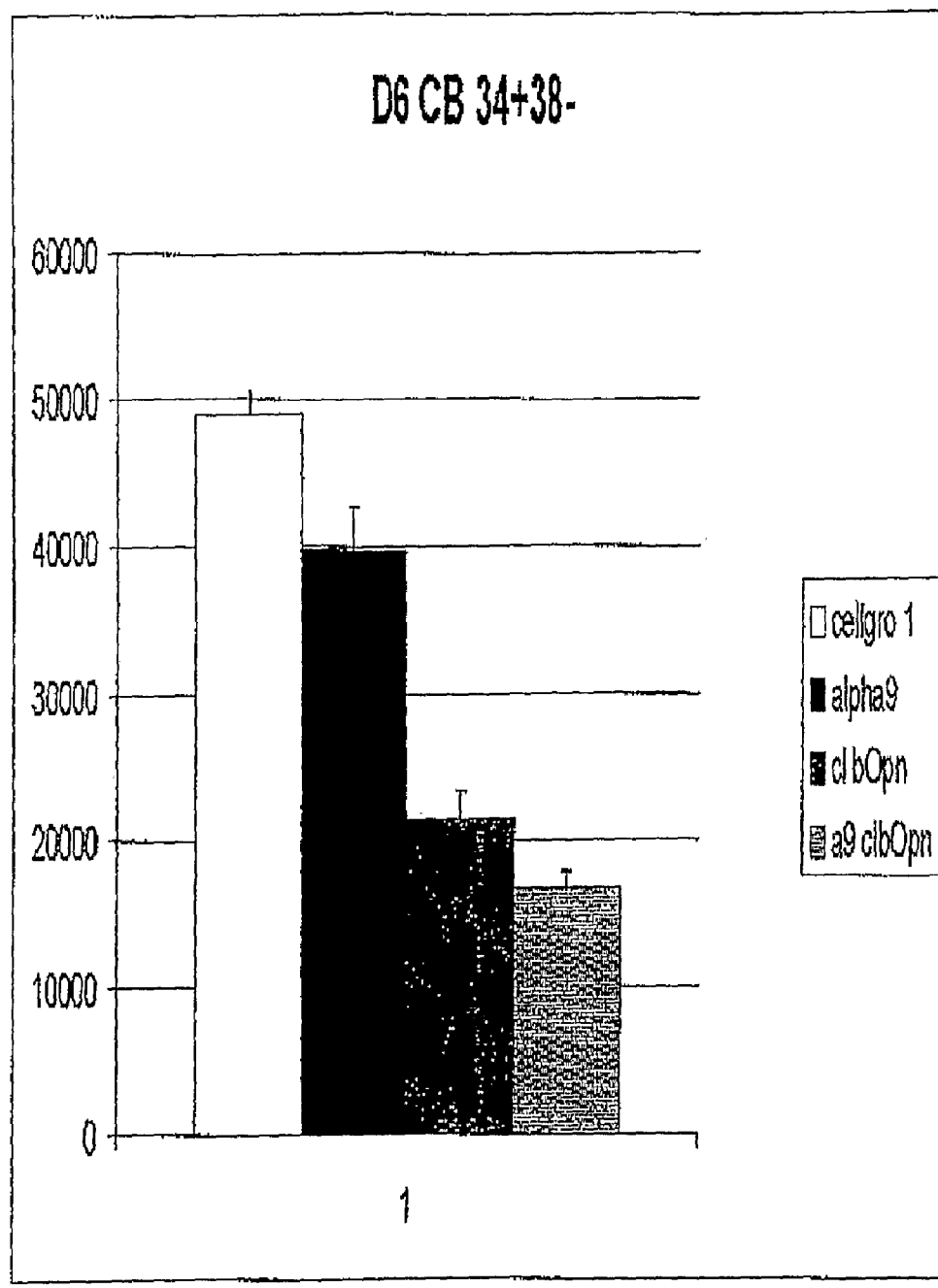
FIG. 3 α9β1 antibody significantly inhibits human hematopoiesis in vitro in the presence of 6 factor stimulation, but not as extensively as thrombin-cleaved Osteopontin—sorted CB CD34$^+$CD38$^-$ HSC (300 per well) were plated in the presence of Cellgro supplemented with 6 factors (white bar), α9β1 antibody (black bar), thrombin cleaved bovine Opn (dark grey bar), and α9β1 antibody with thrombin cleaved bovine Opn (light grey bar). After 6d there was significant inhibition of cell proliferation in the presence of α9β1 antibody and additive effect in the additional presence of cleaved bovine Opn. Data are the mean±SEM of quadruplicate cells.

The results are shown in FIG. 3, Cellgro (white bar), α9β1 antibody (black bar), thrombin cleaved bovine Opn (dark grey bar) and the combination of α9β1 antibody with thrombin cleaved bovine Opn (light grey bar).

After 6 days in culture, cell proliferation of CD34$^+$, CD38$^-$, CB was inhibited in the presence of α9β1 antibody and an additive effect was seen with the addition of cleaved bovine Opn.

Example 3

An Opn Peptide which Binds to α9β1 Significantly Inhibits Human Hematopoiesis in vitro Thrombin-cleaved Opn was prepared by incubating 24 µg bovine Opn in 20 mM Tris-HCl (pH 7.6), 80 mM NaCl, 2 mM CaCl$_2$ and 0.1 units of thrombin (CSL, Parkville, Australia), for 10 min at 37° C. Cleavage or Opn was confirmed by Western blot analysis revealing the 2 expected fragments of approximately 28 and 30 kD.

Figure 4:
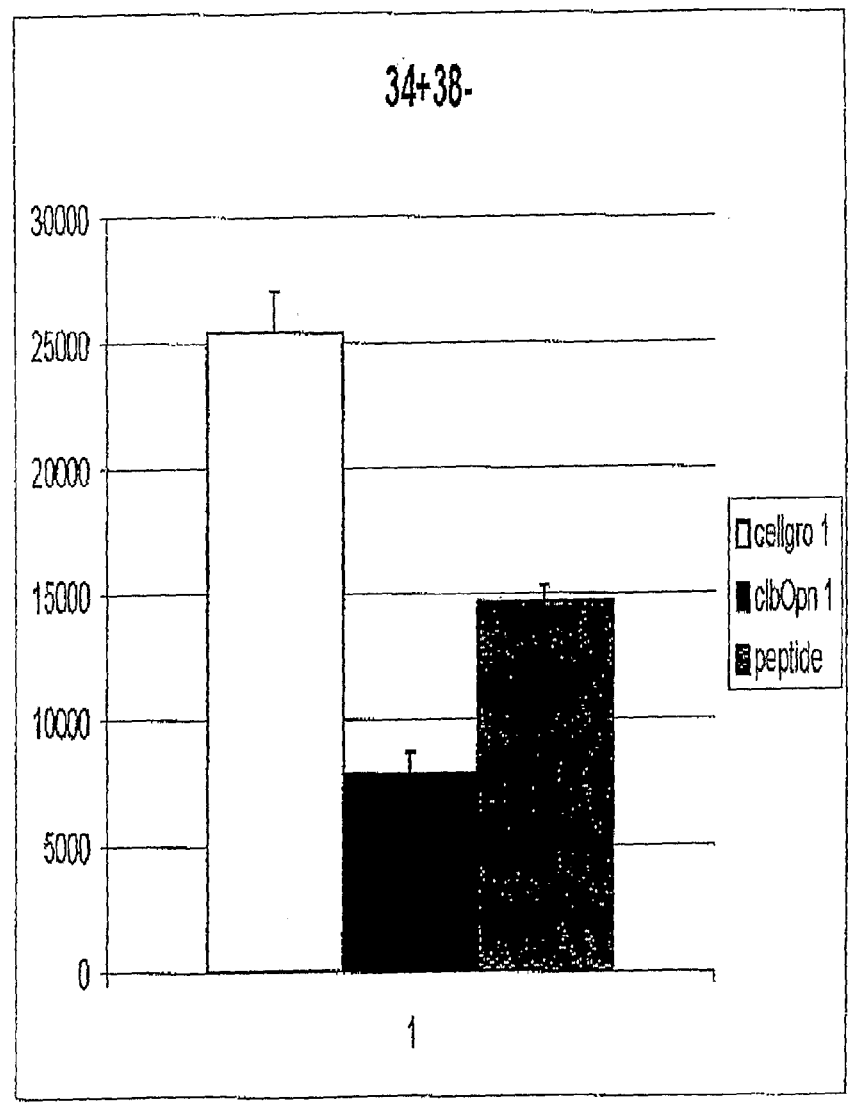
FIG. 4 An osteopontin peptide specific to the region revealed post thrombin cleavage, which binds to α9β1, significantly inhibits human hematopoiesis in vitro in the presence of 6 factor stimulation—sorted CB CD34$^+$CD38$^-$ HSC (300 per well) were plated in the presence of Cellgro supplemented with 6 factors (white bar), thrombin cleaved bovine Opn (black bar), or osteopontin peptide (dark grey bar). After 6d there was significant inhibition of cell proliferation in the presence of thrombin cleaved bovine Opn and osteopontin peptide. Data are the mean±SEM of quadruplicate wells.

Cord blood cells (CD34$^+$, CD38$^-$, HSC) were sorted by fluorescence activated cell sorting (FACS) and plated into cell culture wells (300 cells/well) in the presence of Cellgro supplemented with 6 growth factors (white bar, FIG. 4), thrombin cleaved bovine Opn (black bar), or osteopontin peptide specific to the region revealed post thrombin cleavage (dark grey bar). After 6 days, there was significant inhibition of cell proliferation in the presence of thrombin cleaved bovine Opn and the osteopontin peptide (FIG. 4)

While the present invention has been described with reference to specific embodiments, it should be understood by those skilled in the art that various changes may be made and equivalents may be substituted without departing from the true spirit and scope of the invention. In addition, many modifications may be made to adapt a particular situation, material, or process to the objective, spirit and scope of the present invention. All such modifications are intended to be within the scope of the invention.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for selecting hematopoietic stem cells (HSCs) comprising:
  (a) providing a starting population of cells comprising HSCs; and
  (b) selecting HSCs within the population by providing α9β1 antibodies; and
  (c) separating HSCs from the starting population of cells by virtue of the α9β1 antibodies binding to α9β1 integrin on cell surfaces of HSCs.

2. A method for producing a self-renewable population of hematopoietic stem cells (HSCs) comprising:
  (a) providing a starting population of cells enriched in HSCs;
  (b) isolating HSCs expressing α9β1 integrin on the cell surface away from the starting population of cells;
  (c) culturing HSCs isolated in step (b) in the α9β1 antibodies; and
  (d) harvesting said population of self-renewable HSCs.

3. The method of claim 1 or claim 2 wherein the α9β1 antibodies are immobilized onto a surface.

4. The method of claim 3 wherein the surface forms the outer layer of a culture device, bead, column or the surface of a bioreactor.

5. The method of claim 1 or claim 2 wherein the method further comprises the step of activating α9β1 integrin on the cell surface of the HSCs.

6. The method of claim 1 or claim 2 wherein the method further comprises the step of selecting HSCs with activated α9β1 integrin from the population of HSCs.

7. An HSC population separated or harvested according to the method of claim 1 or claim 2.

* * * * *